United States Patent
Lowden et al.

(10) Patent No.: US 6,246,235 B1
(45) Date of Patent: Jun. 12, 2001

(54) TUBULAR PRODUCTS INSPECTION

(75) Inventors: Donald E. Lowden, Birmingham; Kenneth W. Sanders, Hueytown, both of AL (US)

(73) Assignee: USX Corporation, Pittsburgh, PA (US)

( * ) Notice: Subject to any disclaimer, the term of this patent is extended or adjusted under 35 U.S.C. 154(b) by 0 days.

(21) Appl. No.: 09/064,334

(22) Filed: Apr. 22, 1998

(51) Int. Cl.[7] .......................... G01N 27/84; G01N 27/72; G01R 33/12
(52) U.S. Cl. ............................ 324/216; 324/227
(58) Field of Search ........................ 324/214, 215, 324/216, 226, 227

(56) References Cited

U.S. PATENT DOCUMENTS

| 3,287,632 | * 11/1966 | Tompkins | 324/227 |
|---|---|---|---|
| 3,763,423 | * 10/1973 | Förster | 324/216 |
| 4,477,776 | 10/1984 | Spierer | 324/227 |
| 5,534,775 | 7/1996 | Lam et al. | 324/216 |

FOREIGN PATENT DOCUMENTS 57-146157   9/1982   (JP).

* cited by examiner

Primary Examiner—Walter E. Snow
(74) Attorney, Agent, or Firm—William L. Krayer

(57) ABSTRACT

An inspection station and process for pipe or other ferromagnetic articles utilizes a generally straight flux field amplifier made of a multi-stranded cable surrounded by non-conducting resin, for inducing transverse lines of magnetic force. The flux field amplifier is surrounded by a coil which is also energized to make longitudinal lines of force; the two types of lines of force are vectored. The pipe or other ferromagnetic article is sprayed with UV-sensitive magnetic particles in a more or less conventional manner to display the vectored lines of force together with any flaws in the metal. The cable core of the flux field amplifier does not need a cooling system and is able to last longer than conventional solid cores.

5 Claims, 4 Drawing Sheets

TUBULAR PRODUCTS INSPECTION

TECHNICAL FIELD

This invention relates to the inspection of steel pipes. More particularly it relates to the use of magnetic field generating devices together with magnetic-responsive particles to reveal flaws in ferromagnetic articles such as pipes.

BACKGROUND OF THE INVENTION

Magnetic lines of force in ferromagnetic articles are normally regular and predictable, and this phenomenon has long been used to reveal flaws as part of an inspection process in the production of such articles as pipes. While some techniques have involved the application of an electric current directly to the article to be inspected, in order to generate magnetic lines of force, this practice has been considered dangerous and has other disadvantages, and accordingly the discussion below is restricted to those techniques and configurations wherein magnetic lines of force are induced by the use of electromagnets or other magnetic field inducing devices which need not touch the scrutinized articles. The reader may be interested, however, in the use of eddy current transducers such as employed by Chickering et al in U.S. Pat. No. 4,862,079 for monitoring wear and thickness in control rods of nuclear reactors.

It is known to use large electromagnets to induce magnetic fields in steel pipes and other articles; iron filings or other magnetic responsive particles are spread on the surface of the articles to reveal the patterns of the magnetic lines of force. (Hereafter, in this description, the term pipes may be used interchangeably with "steel pipes and other articles", as it is clear that magnetic-responsive articles other than steel pipes may be inspected in the same or a similar manner). Placement of the pipe in the magnetic field of an electromagnet causes the lines of magnetic force to pass through the pipe in predictable patterns which, however, are distorted by flaws; the distortions are made clearly visible in disruptions of the patterns of the magnetic particles. Commonly, the particles are colored or coated to reflect ultraviolet light.

To complete the saturation of the test piece with magnetic lines of force, it has been known to use both longitudinal and transverse magnetizing devices. That is, a longitudinal magnetic field is induced typically by electromagnetic coils around the pipe (but not touching it) and the transverse, or orthogonal, field is induced by devices in which the axis between the north and south poles is oriented to be more or less parallel to the pipe.

While solid cores work well in magnetic flux amplifiers, they create hazards such as possible shock and arc burns; they also tend to heat up, reducing their efficiency unless a cooling system is used. If no cooling system is used, the core may burn out prematurely.

Spierer, in U.S. Pat. No. 4,477,776, illustrates several different configurations of magnets around a test piece, including one in FIG. 4 in which the longitudinal field is "vectored" by placing the poles of the magnet in positions other than directly across the test piece. He uses both transverse and longitudinal fields, but does not use magnetic particles, relying instead on magnetic sensing means which generate output signals.

In U.S. Pat. No. 4,694,247, Meili et al rotate and advance the pipe on a bed of dry magnetic particles while the pipe is subjected to magnetization.

Jenks, in U.S. Pat. No. 4,931,731, like Spierer in the patent mentioned above, uses both longitudinal and transverse magnetic fields; unlike Spierer, he reads the flaws by observing disturbances in the resulting patterns of magnetic particles. He employs a particular circuitry for maintaining a predetermined balance between the two magnetic fields. See also Kamimura in Japanese application 56-31557. Both Jenks and Kamimura employ two coils to generate the longitudinal field.

Two coils are also used by Lam in U.S. Pat. No. 5,534,775 to generate the longitudinal field. Lam uses "time-varying" magnetic fields, and passes the current through the two coils in directions which tend to cancel the lines of force which do not contribute to the longitudinal field.

Many of the prior art constructions are bulky and difficult to use in the environment of a production plant. It is desirable to keep the inspection process simple while still thorough.

SUMMARY OF THE INVENTION

Briefly, the inventors designed an apparatus and process for inducing a magnetic field in a pipe to be inspected, and thereafter inspecting the pipe for flaws. The invention is designed to be used primarily on the ends of relatively long pipe.

An end of the pipe is brought to rest just above a magnetizing module designed for the purpose, which is typically about 48 inches long. The magnetizing module and the pipe are encircled by a single coil. In order to induce a magnetic field in the pipe, both the magnetizing module and the coil are energized. The magnetizing module will tend to generate a circular, or transverse, magnetic field concentric with the pipe for approximately the length of the module. The coil will tend to generate a longitudinal magnetic field, running in the direction of the pipe.

Because the two units are energized together, they make a composite, vectored, magnetic field—that is, the composite magnetic field is neither orthogonal to the pipe nor parallel to it, but is helically skewed as a function of differences in the strength of the currents used in the module and the coil. In practice, vectoring skews the magnetic lines of force through angles of up to 70° from the orthogonal, more commonly through 20° on each side of the orthogonal, but can be easily done through 360°.

Various combinations of timing and strength of current may be used to achieve various vectoring effects.

Either at the same time the pipe end is being magnetized, or just before or just after, it is sprayed in a more or less conventional manner with a slurry of colored or UV-sensitive magnetized powder or particles which are capable of forming themselves in the patterns of the magnetic lines of force. It may be sprayed inside as well as outside. The pipe need not be rotated at this stage. The pipe, having been magnetized and containing a residual, composite, vectored magnetic field, is then transported to an inspection booth for inspection of the magnetized end. At the inspection booth, the inspector is able to inspect one end of the pipe with a completely unobstructed view, since there is no structure around at all other than the walls of the booth, which may be used to keep out extraneous light. The pipe is rotated and he looks inside the pipe as well as outside. Flaws which are perpendicular to the pipe axis are more easily seen than with other systems because the magnetic field is vectored.

For inspection of the other end of the pipe, it is transported to a second processing area, where the other end is first magnetized in the same manner as above and then placed in a second inspection booth to receive a similar inspection.

The unique magnetizing module used for the imposing the originally transverse magnetic lines of force has a core of tinned copper electrical cable made of at least 1000 strands; generally, for an industrial pipe mill capable of handling pipe of about 26 to about 50 feet in length and varying in diameter from 4 to 11 inches, a core of tinned copper electrical cable having at least 1400 strands is preferred. The upper limit on the number of strands will be dictated as much by economics as by technical effect; generally more than 2000 strands is not necessary. The cable is manufactured or cut to the desired length for the end segment to be inspected, in our case preferably 48 inches. It is encased in a non-magnetic insulating jacket and sealed in a waterproof compound. While we find the most convenient geometry for the module is a straight unit adapted for placement of the pipe above it, many other configurations could be used so long as the operator is able to utilize the resulting patterns of magnetic lines of force.

BRIEF DESCRIPTION OF THE DRAWINGS

A preferred version of the invention will be described with reference to the drawings, in which.

DETAILED DESCRIPTION OF THE INVENTION

There are three basic aspects to our invention—the inducement of a magnetic field in one end of the pipe, movement of the pipe to an inspection station, and the inspection of the magnetized end, which takes place in the inspection station. The process is repeated for the other end of the pipe in separate magnetizing and inspection stations.

Figure 1A:
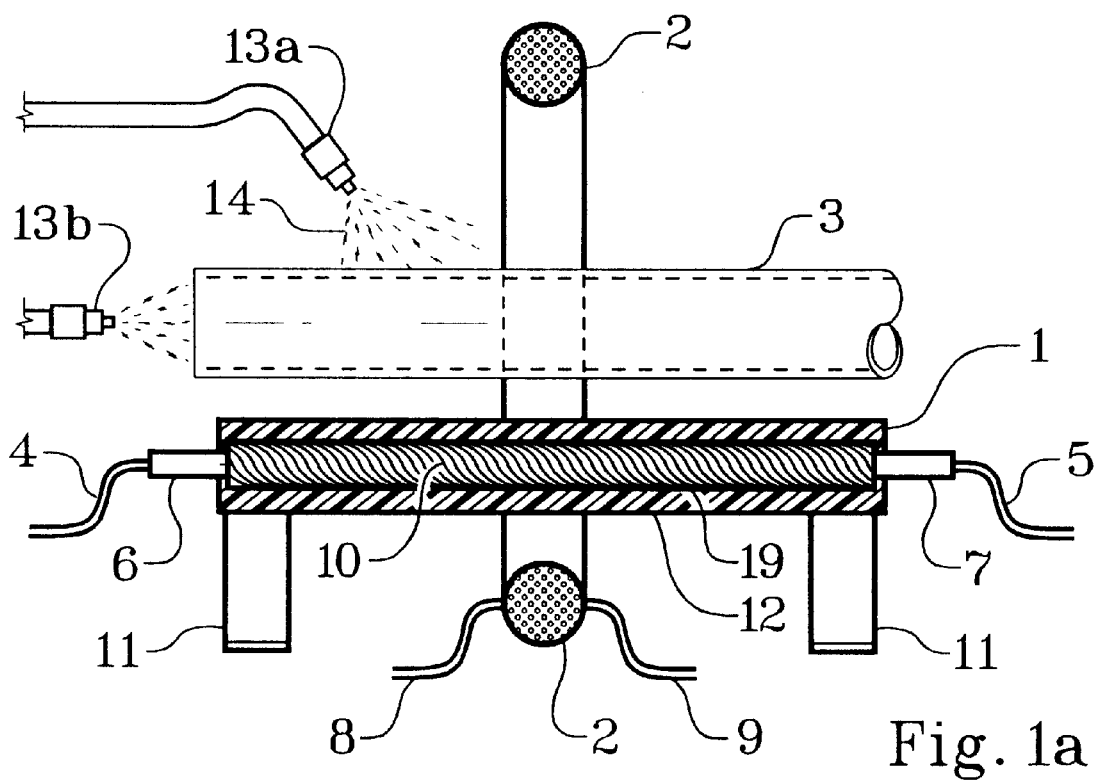
FIGS. 1a, 1b, and 1c are more or less diagrammatic side sectional, overhead and transverse sectional views of the magnetizing station.
Figure 1B:
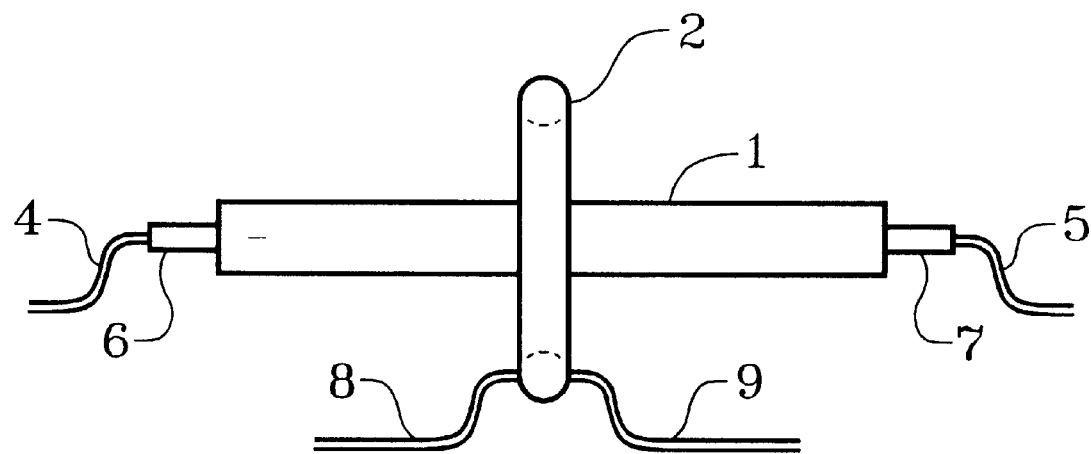
Figure 1C:
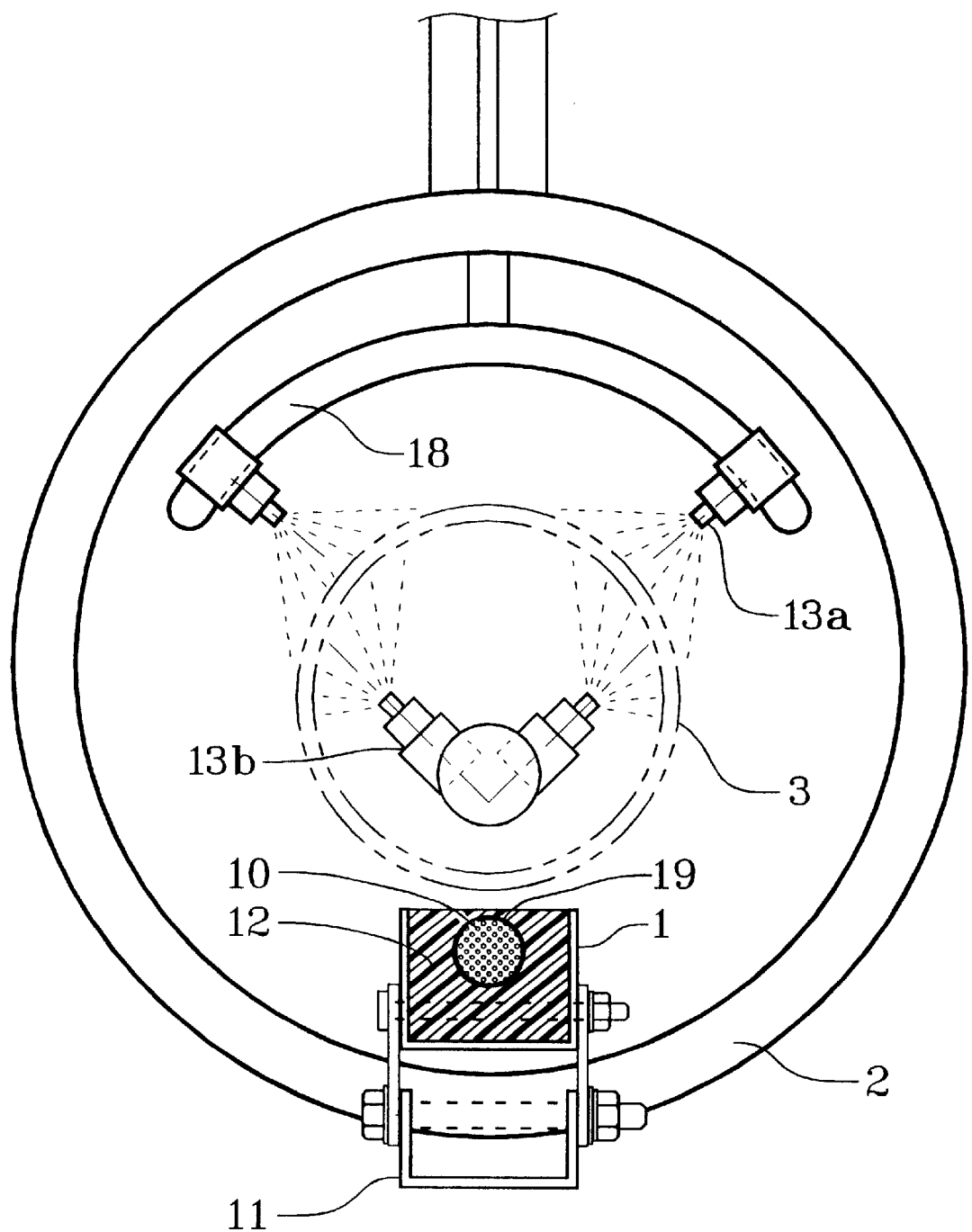

The inducement of the magnetic field in the pipe takes place in a magnetizing station, which is illustrated in FIGS. 1a, 1b, and 1c. Movement of the pipe from a magnetizing station to an inspection station, and provision for inspection of both ends of a pipe, are described with reference to FIG. 2.

Our invention includes the unique magnetizing module illustrated in FIGS. 1a, 1b, and 1c as part of the magnetizing station.

Referring now to FIG. 1a, which is a side, partially sectional, view of the magnetizing station, the magnetizing station comprises a transverse magnetizing module 1 for inducing lines of force orthogonal to the pipe 3 and a coil 2 surrounding both the magnetizing module and the pipe 3 for inducing lines of force longitudinal to the pipe 3. Pipe 3 is positioned over and approximately parallel to magnetizing module 1. Magnetizing module 1, supported by legs 11, has terminals 6 and 7 for connection to power conductors 4 and 5 and a power source not shown. Coil 2 is also connected to a power source, through terminals 8 and 9. The steel pipe 3 or other ferromagnetic article to be inspected is placed over and generally parallel to magnetizing module 1, and passes through coil 2. Exterior spray nozzle 13a is positioned to spray a slurry 14 of magnetic particles on the exterior of pipe 3 and interior spray nozzle 13b is positioned for insertion into the pipe 3 to coat the interior with a similar slurry. For an industrial or oilfield pipe manufacturing facility in which the pipe is typically about 26 feet to about 50 feet long, magnetizing module 1 is desirably about 48 inches long, but may vary in length from about 2 feet to about 6 feet; the diameter of the pipe 3 is usually about 4 inches to about 11 inches, but may vary from about 2 inches to about 14 inches, and accordingly the magnetizing station should be able to accommodate such variations. Our invention contemplates handling and inspecting pipe of lengths from about 26 feet to about 50 feet; desirably there will be a separate magnetizing station for each end of the pipe, as is illustrated elsewhere herein.

Magnetizing module 1 is seen to comprise a cable 19 having numerous strands 10 surrounded by a non-conducting resin 12. Conceptually, i.e. including both small and large industrial installations, the cable 19 may range in size from 1/0 to 1111 MCM. For our purposes in a pipe mill, we prefer a cable of 545 MCM. "MCM" is a commercial term meaning one thousand circular mils.

In FIG. 1a, the cable 19 and protective resin 12 of magnetizing module 1 comprises a flux field amplifier, wherein the cable 19 is made up of numerous wires, i.e. strands 12, preferably of copper and preferably having a tin coating. Cable 19 is therefore essentially a copper cable having at least 1325 strands, normally helically disposed, but not essentially so. Surrounding cable 19 is an insulating compound or resin 12 for containing the current in the cable 19 while permitting the desired magnetic induction action. Terminals 6 and 7 may be marked positive and negative, but these positions may be reversed. Three-phase rectified AC is used for the magnetizing process. Approximately 4000 Amps of current at 60 to 80 volts DC (half wave) at a duration of 1.5 to 2.5 seconds is used for the process. Half wave current in a non-contact process provides the most effective means of magnetizing an article without the need to worry about time varying electronic controls.

In FIG. 1b, an overhead view, the coil 2 is shown approximately in the center of magnetizing module 1.

As emphasized in the transverse view of FIG. 1c, the coil 2 surrounds both the magnetizing module 1 and pipe 3, preferably without touching either. In this view, interior spray nozzle 13b is shown inside pipe 3 exterior spray nozzle 13a is served by header 18.

Figure 2:
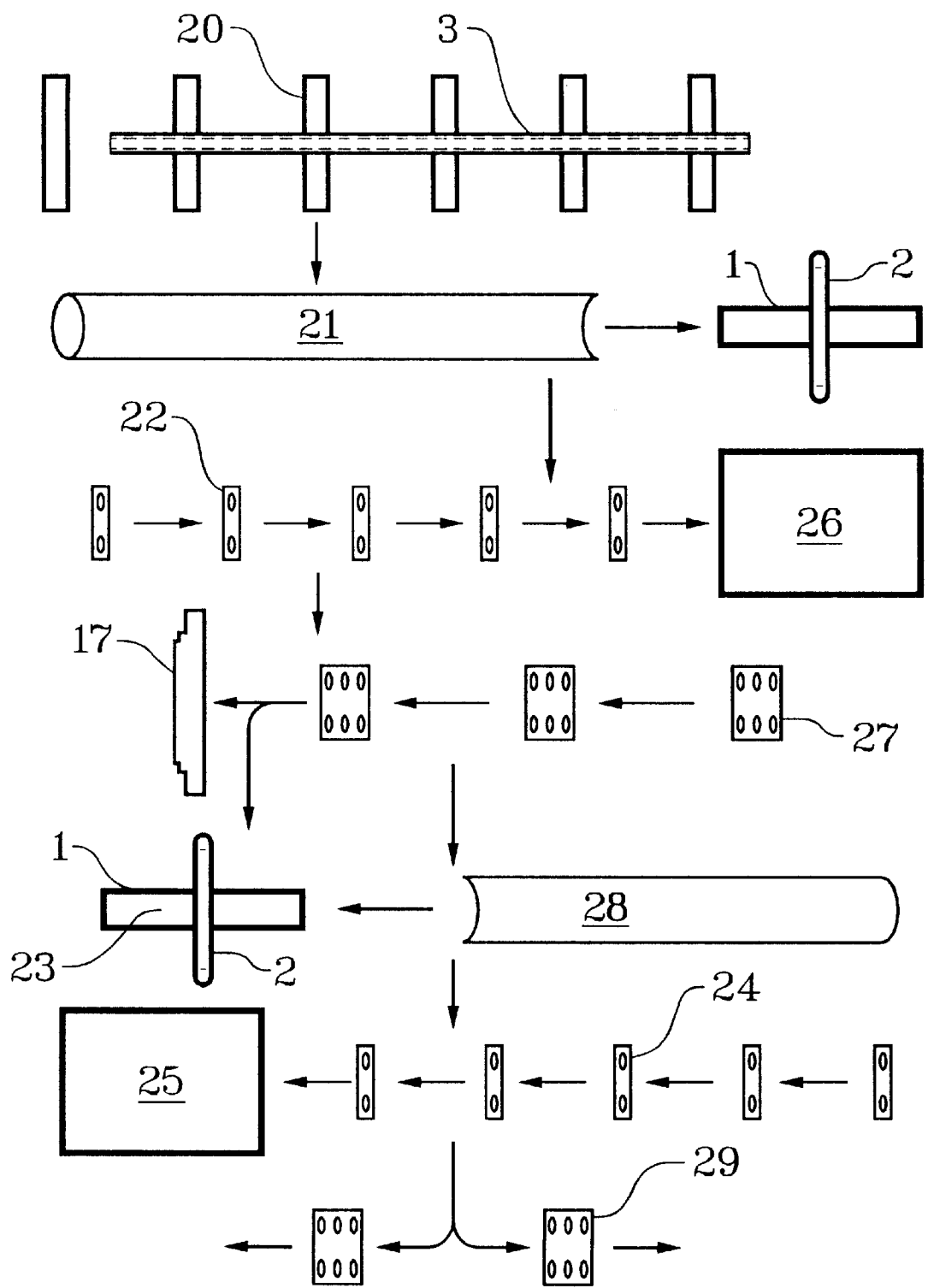
FIG. 2 is a more or less diagrammatic floor layout for the process, showing first and second magnetizing stations, and first and second inspection areas.

FIG. 2 is an overhead view of a more or less diagrammatic floor layout of the overall process. A pipe 3 begins at initial station 20 and is moved by a walking beam not shown to the initial support or trough 21 which holds an end of the pipe 3 over magnetizing module 1 and inside coil 2 as illustrated in FIGS. 1a, 1b, and 1c while it is magnetized. Carrying its residual magnetization, it is moved to rolls 22 which support it for inspection in inspection booth 26. Ordinary light may be largely excluded from the inspection booth 26.

Sources of ultraviolet light (not shown) are energized, and the inspector may rotate the pipe 3 on rolls 22 to observe deviations in the regular patterns of the UV-sensitive material on the surfaces. After inspection, the pipe may be moved longitudinally (to the left, as depicted) by shuttle rolls 27 and may be aligned by alignment bumper 17, for magnetization on the second magnetizing module 23, where the same procedure is followed as described for FIGS. 1a, 1b, and 1c. The pipe is transferred to support rolls 24 which may rotate the pipe 3 while the left end of the pipe (as depicted) is inspected in inspection booth 25. After marking, the pipe may be routed on rolls such as rolls 29 in different directions depending on the types and locations of the flaws, if any.

Ultraviolet-sensitive magnetic particles from the sprayed slurry 14 are illuminated by a series of UV lights which are positioned above the outside diameter of the article and as it is rotated, the outside surface of the pipe is visually inspected for a buildup of particles which would be drawn into any break in the magnetic field. The pipe is rotated at least one revolution for the outside inspection. The operator can also stop the rotation at any point to make a determination as to whether a defect is present. After inspection of the outside of the pipe, the inspector inspects the inside for at least one revolution. This is done with an UV light so as to illuminate the inside surface of the pipe and is adjustable to accommodate various pipe diameters, as well as the individual inspector's preference for specific angles necessary to carry out the inspection. Approximately 48 inches of the end of the pipe to be inspected. The inspection station is preferably closed or insulated from outside sources of light which might reduce the efficiency of the UV system.

Figure 3:
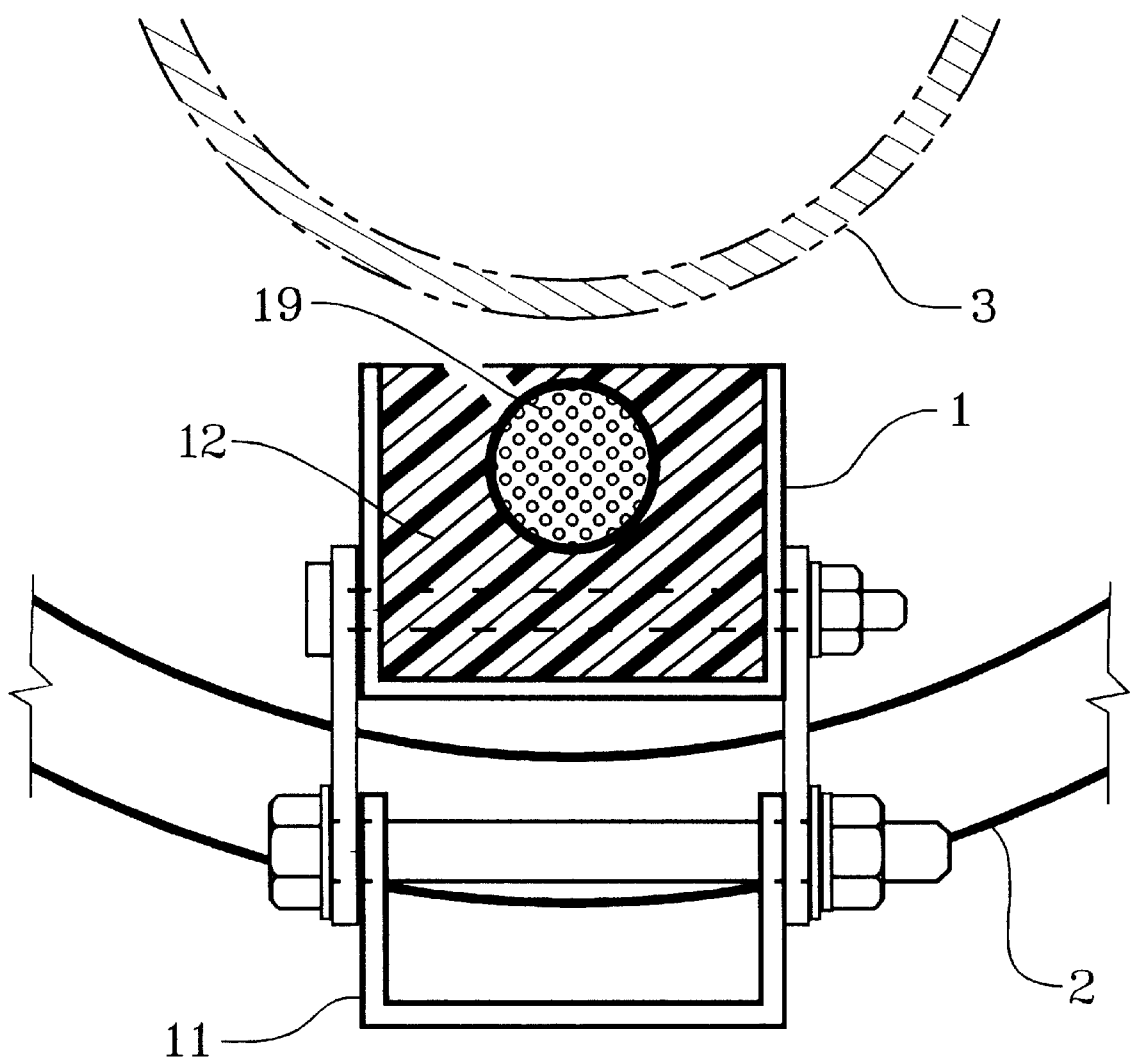
FIG. 3 is an expanded sectional view of the magnetizing module.

In FIG. 3, details are shown of the flux field amplifier. Cable 19 is embedded in resin 12 and pipe 3 is positioned just above it. Strands 10 of cable 19 are better able to dissipate heat than a solid core, and they accelerate the development of the magnetic field—as the current passes through the strands 10, each one develops its own magnetic field, which is amplified by the other strands, building one upon another.

The controls of the process are arranged to permit manipulation of the vectoring of the magnetization. That is, current may be supplied to varying numbers of strands and/or coil wraps, and through strands of different diameters. Varying the ratios of the currents and of the voltages between the coil and the magnetizing module also affects vectoring. Vectoring is the imposition of two incongruent fields into an article at the same time with different current and voltage levels and/or otherwise influenced to have different field strengths. In the literature, a variable field may also be known as a "swinging field", which may rotate throughout 360°. The distance (air gap) from the pipe is also a determining factor in the strength of the vectored array, and the distance will influence the convenience of depositing the magnetic particles on the pipe. Thus vectoring is influenced both by the physical structure of the apparatus and by the application of current to the two types of magnetic field generators.

The magnetic particles are well known in the art. We may use any of the common commercial magnetic particles, preferably ones of iron or iron oxide treated with a fluorecent pigment or otherwise made readily reflective of ultraviolet light.

Periodically, magnetic flux indicator strips (also known to the art) may be applied to the inside and outside of the pipe to test for field strength. Even when the magnetic flux indicator strips are used, the inspector still looks for flaws by observing the patterns of magnetic particles applied by spraying. Vectoring effects can be shown using these strips and correlated to the power programming for the magnetizing module and the coil.

Our invention is not limited to the above particular variations and embodiments. For example, the use of the magnetizing module need not be limited to the ends of pipes; rather, one or more magnetizing modules may be utilized in the central areas of the pipes between the ends. Nor is it essential to restrict the inspection process to the particular sequence of steps described—for example, the magnetizing modules and inspection booths may be so arranged as to permit simultaneous magnetization of the ends, and simultaneous inspection. Likewise, if magnetizing modules are used in central segments of the pipe as well as end areas, all may be energized at the same time or sequentially, according to the operator's preference or other dictates.

What is claimed is:

1. An inspection system for an elongated ferromagnetic article having two end portions comprising:
    (a) a first magnetizing station comprising a first flux field amplifier comprising a multi-stranded cable for inducing magnetic lines of force transverse to a first end portion of said elongated ferromagnetic article, a first coil for inducing magnetic lines of force longitudinal to said first end portion of said elongated ferromagnetic article, and a first particle spray apparatus for spraying magnetic particles on said first end portion of said elongated ferromagnetic article,
    (b) a first inspection zone for inspecting said first end portion of said elongated ferromagnetic article,
    (c) a second magnetizing station comprising a second flux field amplifier comprising a multi-stranded cable for inducing magnetic lines of force transverse to a second end portion of said elongated ferromagnetic article, a second coil for inducing magnetic lines of force longitudinal to said second end portion of said elongated ferromagnetic article, and a second particle spray apparatus for spraying magnetic particles on said second end portion of said elongated ferromagnetic article, and
    (d) a second inspection zone for inspecting said second end portion of said elongated ferromagnetic article.

2. An inspection system of claim 1 wherein said first and second inspection zones include apparatus for rotating said elongated ferromagnetic article.

3. An inspection system of claim 1 wherein said magnetic particles are treated to reflect ultraviolet light and said inspection zones include means for generating ultraviolet light.

4. Method of inspecting pipe comprising:
    (a) in a first magnetizing zone, inducing a vectored magnetic field in a first end portion of said pipe by the application of electric current to transverse and longitudinal magnetic field inducing modules therefor,
    (b) before, during, or after said application of electric current, spraying magnetic particles on said first end portion of said pipe to display said vectored magnetic field,
    (c) terminating the application of electric power to said magnetic field inducing modules,
    (d) moving said pipe to a first inspection zone,
    (e) while said magnetic field is retained therein, inspecting said first end portion of said pipe in said first inspection zone by observing the deployment of said magnetic particles on said pipe,
    (f) moving said pipe to a second magnetizing zone,
    (g) in said second magnetizing zone, inducing a vectored magnetic filed in a second end portion of said pipe by the application of electric current to transverse and longitudinal magnetic field inducing modules therefor,
    (h) terminating the application of electric power to said magnetic field inducing modules, and
    (i) while said magnetic field is retained therein, inspecting said second end portion of said pipe in said second inspection zone by observing the deployment of said magnetic particles.

5. Method of claim 4 wherein said vectored magnetic field is induced by simultaneously generating longitudinal and transverse magnetic fields.

* * * * *